US008329776B2

(12) United States Patent  
Hecht et al.

(10) Patent No.: US 8,329,776 B2  
(45) Date of Patent: Dec. 11, 2012

(54) DENTAL COMPOSITION CONTAINING A POLYFUNCTIONAL (METH)ACRYLATE COMPRISING URETHANE, UREA OR AMIDE GROUPS, METHOD OF PRODUCTION AND USE THEREOF

(75) Inventors: Reinhold Hecht, Kaufering (DE); Uwe H. Hoheisel, Türkenfeld (DE); Christoph Thalacker, Weilheim (DE); William J. Schultz, North Oaks, MN (US); Wendy L. Thompson, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 30 days.

(21) Appl. No.: 12/666,833

(22) PCT Filed: Jun. 27, 2008

(86) PCT No.: PCT/US2008/068536  
§ 371 (c)(1),  
(2), (4) Date: Nov. 16, 2010

(87) PCT Pub. No.: WO2009/006282  
PCT Pub. Date: Jan. 8, 2009

(65) Prior Publication Data  
US 2011/0053116 A1 Mar. 3, 2011

(30) Foreign Application Priority Data  
Jun. 29, 2007 (EP) .................................... 07111356

(51) Int. Cl.  
*A61K 6/083* (2006.01)  
*A61C 5/00* (2006.01)  
*C08G 18/04* (2006.01)

(52) U.S. Cl. .......... 523/116; 523/118; 528/73; 540/202; 433/228.1

(58) Field of Classification Search .................... 528/73; 540/202; 433/228.1; 523/118, 116  
See application file for complete search history.

(56) References Cited

U.S. PATENT DOCUMENTS

| 3,347,954 | A | * | 10/1967 | Bredereck et al. ............... 525/21 |
| 3,541,068 | A | * | 11/1970 | Taylor ............................ 523/116 |
| 3,729,313 | A | * | 4/1973 | Smith ............................ 430/332 |
| 3,741,769 | A | * | 6/1973 | Smith ............................ 522/25 |
| 3,808,006 | A | * | 4/1974 | Smith ........................ 430/495.1 |
| 3,825,518 | A | * | 7/1974 | Foster ............................ 523/116 |
| 4,071,424 | A | * | 1/1978 | Dart et al. ....................... 522/14 |
| 4,145,544 | A | * | 3/1979 | Kuehn ............................ 544/222 |
| 4,159,376 | A | * | 6/1979 | Kuehn ............................ 544/222 |
| 4,250,053 | A | * | 2/1981 | Smith ............................ 502/167 |
| 4,328,325 | A | * | 5/1982 | Marquardt et al. ............. 525/451 |
| 4,394,403 | A | * | 7/1983 | Smith ............................ 427/500 |
| 4,443,587 | A | * | 4/1984 | Schmitt et al. ................. 526/146 |
| 4,544,742 | A | * | 10/1985 | Schmitt et al. ...................... 544/8 |
| 4,642,126 | A | * | 2/1987 | Zador et al. ...................... 51/295 |
| 4,648,843 | A | * | 3/1987 | Mitra .......................... 433/201.1 |
| 4,652,274 | A | * | 3/1987 | Boettcher et al. ............... 51/298 |
| 4,737,593 | A | * | 4/1988 | Ellrich et al. .................... 568/15 |
| 4,762,863 | A | * | 8/1988 | Sasaki et al. .................... 522/11 |
| 4,772,530 | A | * | 9/1988 | Gottschalk et al. ........... 430/138 |
| 4,787,850 | A | * | 11/1988 | Michl et al. ................. 433/201.1 |
| 4,795,823 | A | * | 1/1989 | Schmitt et al. ................. 560/182 |
| 4,855,334 | A | * | 8/1989 | Maruyama et al. ............. 522/96 |
| 4,874,450 | A | * | 10/1989 | Gottschalk ................. 156/275.5 |
| 4,933,376 | A | * | 6/1990 | Sasaki et al. .................... 522/14 |
| 4,954,414 | A | * | 9/1990 | Adair et al. .................... 430/138 |
| 4,977,197 | A | * | 12/1990 | Sasaki et al. .................... 522/14 |
| 5,055,372 | A | * | 10/1991 | Shanklin et al. .............. 430/138 |
| 5,057,393 | A | * | 10/1991 | Shanklin et al. .............. 430/138 |
| 5,182,332 | A | * | 1/1993 | Yamamoto et al. ........... 523/115 |
| 5,296,513 | A | * | 3/1994 | Ige et al. ........................ 523/115 |
| 5,302,630 | A | * | 4/1994 | Mukai et al. .................. 523/118 |
| 5,332,429 | A | * | 7/1994 | Mitra et al. ..................... 106/35 |
| 5,545,676 | A | * | 8/1996 | Palazzotto et al. ............. 522/15 |
| 5,719,227 | A | * | 2/1998 | Rosenberry et al. .......... 524/590 |
| 5,843,576 | A | * | 12/1998 | Rosenberry et al. ....... 428/423.1 |

(Continued)

FOREIGN PATENT DOCUMENTS

| DE | 1495520 | 4/1969 |
| DE | 19928238 | 12/2000 |
| EP | 0059451 | 9/1982 |
| EP | 0209365 | 1/1987 |
| EP | 0235826 | 9/1987 |
| EP | 934926 | 8/1999 |

OTHER PUBLICATIONS

Mitra, "Dental Composites Prepared from Resin Matrices Containing Ethylenically Unsaturated Carbamoyl Isocyanurates", Polymer Preprints, Division of Polymer Chemistry, American Chemical Society, vol. 38, No. 2, pp. 103-104. XP008085102.  
European Search Report for PCT Application 07111356.7 1219, 10 pages.  
Written Opinion of the ISA for International Application No. PCT/US2008/068536, 7 pgs.  
International Search Report for PCT/US2008/068536, 4 pages.

*Primary Examiner* — James J Seidleck  
*Assistant Examiner* — Peter A Salamon  
(74) *Attorney, Agent, or Firm* — Stephen L. Crooks

(57) ABSTRACT

The invention relates to a dental composition comprising a) a hardenable compound (A1), b) a filler (B1), c) an initiator (C1) being able to initiate curing of compound (A1), compound (A1) having the structure A-(-S1-U-S2-MA)$_n$, with A being a connector element, S1 being a spacergroup comprised of units connected with each other and comprising at least 4 units, S2 being a spacergroup comprised of units connected with each other and comprising at least 4 units, U being an urethane, an amide or an urea group connecting spacergroups S1 and S2, MA being an acrylate or methacrylate group and n being 3 to 6. The invention also relates to a process of producing this dental composition and using the dental composition e.g. as a temporary and/or long term crown and bridge material.

14 Claims, No Drawings

U.S. PATENT DOCUMENTS

| | | | |
|---|---|---|---|
| 5,918,772 A * | 7/1999 | Keller et al. | 222/145.6 |
| 5,944,419 A * | 8/1999 | Streiff | 366/337 |
| 5,998,561 A * | 12/1999 | Jada | 528/15 |
| 6,332,991 B1 * | 12/2001 | Assi et al. | 264/16 |
| 6,482,869 B1 * | 11/2002 | Bolte et al. | 522/35 |
| 6,653,375 B2 * | 11/2003 | Moszner et al. | 524/116 |
| 6,777,458 B1 * | 8/2004 | Jaworek et al. | 522/1 |
| 6,787,197 B1 * | 9/2004 | Jaworek et al. | 427/508 |
| 6,852,775 B1 * | 2/2005 | Soglowek et al. | 523/109 |
| 6,899,948 B2 * | 5/2005 | Zhang et al. | 428/331 |
| 7,078,446 B2 * | 7/2006 | Moszner et al. | 523/116 |
| 2002/0082315 A1 * | 6/2002 | Moszner et al. | 523/106 |
| 2003/0008967 A1 * | 1/2003 | Hecht et al. | 524/507 |
| 2003/0187091 A1 * | 10/2003 | Moszner et al. | 523/116 |
| 2006/0187752 A1 * | 8/2006 | Keller | 366/337 |
| 2007/0090079 A1 * | 4/2007 | Kelller | 215/211 |

* cited by examiner

DENTAL COMPOSITION CONTAINING A POLYFUNCTIONAL (METH)ACRYLATE COMPRISING URETHANE, UREA OR AMIDE GROUPS, METHOD OF PRODUCTION AND USE THEREOF

CROSS REFERENCE TO RELATED APPLICATIONS

This application is a national stage filing under 35 U.S.C. §371 of PCT/US2008/068536, filed Jun. 27, 2008, which claims priority to EP Application No. 07111356.7, filed Jun. 29, 2007, the disclosure of which is incorporated by reference in its entirety herein.

FIELD OF THE INVENTION

The invention relates to a dental composition comprising polyfunctional (meth)acrylates containing urethane, urea or amide groups, a process for producing it and a method of using it including the manufacturing of temporary and long term crown and bridge materials.

BACKGROUND ART

U.S. Pat. No. 4,648,843 relates to method of dental treatment using poly(ethylenically unsaturated) carbamoyl isocyanurates and dental materials made therewith. A similar approach is described by Sumita B. Mitra in "Dental composites prepared from resin matrices containing ethylencially unsaturated carbamoyl isocyanorates in Polymer Preprints, Division of Polymer Chemistry, American Chemical Society, vol. 38, no. 2. pages 103-140.

In U.S. Pat. No. 4,787,850 a two stage process for producing artifical teeth or crowns or inlays is described using a polyfunctional polyisocyanate, a polyol, a methacrylate monomer containing hydroxyl groups and a catalyst.

U.S. Pat. No. 7,078,446 B2 refers to a (meth)acrylate substituted iminooxadiazindione derivative and its use for the production of dental compositions.

EP 0 934 926 A1 relates to an urethane di(meth)acrylate derivative of 1.3 bis(1-isocyanato-1-methylethyl)benzene and its use for the production of dental materials.

It is stated that some of the compositions described in the background art above can be used for the production of dental crown and bridge materials in view of their mechanical properties.

However, there is still room for improvement especially with regard to the requirements to be fulfilled with respect to modern dental materials. Some of the materials are too hard and too brittle some of them are too flexible.

Patients and dentists nowadays have an increasing demand for long term stability of the temporary materials.

Thus, there is still a need for an improved dental composition, which can be used inter alia as a temporary or long term crown and bridge material.

DESCRIPTION OF THE INVENTION

In one embodiment the present invention features a dental composition comprising
a) a hardenable compound (A1),
b) a filler (B1) and
c) an initiator (C1) being able to initiate curing of compound (A1), compound (A1) having the structure A-(-S1-U-S2-MA)$_n$, with
A being a connector element comprising at least one unit,
S1 being a spacergroup comprising at least 4 units connected with each other,
S2 being a spacergroup comprising at least 4 units connected with each other,
the units of A, S1 and S2 being independently selected from $CH_3-$, $-CH_2-$, $-O-$, $-S-$, $-NR^1-$, $-CO-$, $-CR^1=$,

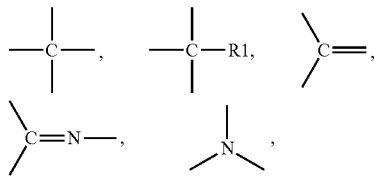

$-N=$, $-CR^1R^2-$,
with $R^1$ and $R^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups,
U being an urethane, urea or amide group connecting spacergroups S1 and S2,
MA being an acrylate or methacrylate group and
n being 3 to 6.

In another embodiment, the invention relates to a process of producing compound (A1) as described in the text of the invention.

A further embodiment of the invention is directed to a method of producing the dental composition.

The invention is also related to a kit of parts and a cartridge containing the components of the inventive composition.

Moreover, the invention features a method of using a hardenable compound (A1) as described in the text of the invention for producing a dental composition.

The invention also relates to a method of producing a temporary or long term crown and bridge, wherein the dental composition of the invention is placed into the negative moulds of a set dental impression material of a tooth structure.

It has been found that the composition described in the text of the invention fulfils the practitioners' needs especially with regard to the balance between hard and flexible properties. Thus, depending on the formulation chosen dental materials with improved fracture resistance can be provided.

Moreover, it has been found that if the dental material contains nano-sized fillers, high strength as well as high translucency can be imparted. Dental materials containing specified amounts of nano-sized silica particles may have desirable handling (e.g. rheological) properties in an uncured state and may show high strength in a cured state combined with good aesthetic characteristics.

Strength can be characterized by mechanical measurements such as impact strength and/or flexural strength. High impact strength in a dental material is advantageous due to the forces exerted by mastication on dental repairs, replacements and restorations. Flexural strength indicates the dental material's ability to withstand compression forces that introduce a tensile stress in the material. Compositions showing well balanced properties especially with respect to impact strength and flexural strength can qualify especially as temporary or long term crown and bridge materials. Tests for each strength measurement are set out below in the Examples. Well balanced properties may also contribute to improving the long term stability of a set dental composition, especially if placed into a patient's mouth.

It has also been found that compositions of the invention, even if filled to a relatively high level with fillers including nano-sized silica particles, still possess good rheological properties. These properties as well as strength can be enhanced by using surface-modifying agents to treat the surface of the particles. Surface treatment (surface-modification) may enhance the dispersibility of the particles and their ability to bind into the matrix.

Furthermore, all components used in the dental composition of the invention are typically biocompatible, that is the composition does not produce a toxic, injurious, or immunological response in living tissue.

Definitions

A "dental composition" within the meaning of the invention is any composition which can be used in the dental field. In this respect the composition should be not detrimental to the patient's health and thus free of hazardous and toxic components being able to migrate out of the composition. Examples of dental compositions include permanent and temporary crown and bridge materials, artificial crowns, anterior or posterior filling materials, adhesives, cements, mill blanks, and orthodontic devices.

A "hardenable compound" within the meaning of the invention is any compound which can be cured or solidified e.g. by chemical crosslinking through radiation-induced polymerization, crosslinking by using a redox initiator or heating.

"Dispersed within the resin" means that filler particles are present in the resin as agglomerated or aggregated or discrete, unassociated (i.e. non-agglomerated and non-aggregated) particles.

A "nano-sized filler" within the meaning of the invention is a filler, the individual particles thereof have a size in the region of nanometers, e.g. an average particle diameter of less than about 200 nm. Useful examples are given in U.S. Pat. No. 6,899,948 B2 the content of which especially with regard to nano-sized silica particles is herein incorporated by reference.

An "initiator" within the meaning of the invention is a substance being able to start the curing process of a hardenable compound.

A "curing or setting reaction" within the meaning of the invention is a reaction wherein physical properties such as viscosity and hardness of a composition changes over the time due to a chemical reaction between the individual components.

A "unit" within the meaning of the invention is a single building block of a chemical molecule or substructure thereof. Single units are connected to each other. Typical units include: $CH_3$—, —$CH_2$—, —O—, —S—, —$NR^1$—, —CO—, —$CR^1$=,

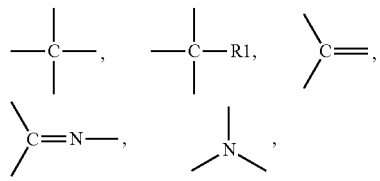

—N=, —$CR^1R^2$—, with $R^1$ and $R^2$ independently selected from hydrogen, linear alkyl groups (including C1, C2, C3, C4, C5 C6 groups), substituted alkyl groups (including C1, C2, C3, C4, C5 C6 groups), alkenyl groups (including C1, C2, C3, C4, C5 C6 groups), cycloalkyl groups (including C4 to C14 groups), substituted cycloalkyl groups (including C4 to C14 groups), arylalkyl groups (including C7 to C20), aryl groups (including C6 to C14) or substituted aryl groups (including C7 to C20). These units can form linear, branched or cyclic structures such as alkyl, cycloalkyl, aryl, ester, urethane or amide groups.

A "connector element" within the meaning of the invention is an element acting as a centre connecting the individual (meth)acrylate containing side chains. The connector element can have a cyclic or branched structure. The connector element can even be a single atom including N. If the connector element has a cyclic structure, it can be a saturated, unsaturated or aromatic homocycle, that is, it comprises only hydrocarbon or substituted hydrocarbon units, or it can be a saturated, unsaturated or aromatic heterocycle, that is, it comprises hydrocarbon or substituted hydrocarbon units and at least one hetero atom including —O—, —N=, —NH—, —$NR^1$— and/or —S—. If the connector element has a branched structure, it comprises a central atom like C or N from which at least three or four individual (meth)acrylate containing side chains are extending. Independently from the chemical structure of the connector element, the arrangement of the individual (meth)acrylate containing side chains with respect to the connector element can be symmetric or asymmetric.

A "spacergroup" within the meaning of the invention is a group connecting at least two other groups in a chemically defined molecule. This group can be a substituted or not substituted carbon chain, which can in addition contain hetero atoms (including O, N and S) or functions like carbonyl groups.

An "urethane group" within the meaning of the invention is a group having the structure —NH—CO—O—.

An "urea group" within the meaning of the invention is a group having the structure

—NH—CO—NH—.

An "amide group" within the meaning of the invention is a group having the structure

—NH—CO—.

A "dental impression material" within the meaning of the invention is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month). A long term crown and bridge material is typically used over a time period of about 6 to 24 months.

DETAILED DESCRIPTION OF THE INVENTION

It has been found that component (A1) and the nature of the filler contribute to the mechanical features of the cured composition. Without wishing to be bound to any theory, it is believed that component (A1) contributes to the improvement of mechanical properties, whereas the filler (B1), especially if it is a nanofiller, contributes to the esthetic properties.

The hardenable compound (A1) of the inventive composition is represented by the structure

with

A being a connector element comprising at least about 1, 2, 3, 4, 5, 6, 7, 8, 9, 10, 11, 12, 13, 14, 15, 16, 17, 18, 19 or 20 units, S1 being a spacergroup comprised of units connected with each other and comprising at least about 4, 5, 6, 7, 8, 9 or 10 units, S2 being a spacergroup comprised of units connected with each other and comprising at least about 4, 5, 6, 7, 8, 9, 10, 12, 15, 20 or 25 units, U being a urethane, urea or amide group connecting spacergroups S1 and S2, MA being an acrylate or methacrylate group and n being about 3 to 6 or about 4 to 6 or about 5 to 6.

It can be preferred, if A has a cyclic structure and comprises at least about 6 units.

It can further be preferred, if S1 has a linear or branched structure and comprises at least about 4 or about 6 units.

It can further be preferred, if S2 has a linear or branched structure and comprises at least about 6 or about 8 units.

It can further be preferred, if U is a urethane group.

A hardenable compound (A1), wherein A has a cyclic structure and comprises at least about 6 units and S1 has a linear structure and comprises at least about 4 units and S2 has a linear structure and comprises at least about 8 units and U is a urethane group can also be preferred.

Within the meaning of the invention, neither the atoms of the urethane, urea or amide group connecting S1 and S2 nor the atoms of the (meth)acrylgroup belong to the spacergroup S1 or S2. Thus, the atoms of the urethane, urea or amide group do not count as units of the spacergroups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S).

Specific examples of connector element A having a cyclic structure include:

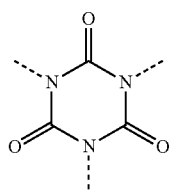

(6 units)

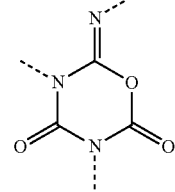

(6 units)

Specific examples of connector element A having a non-cyclic but branched structure include:

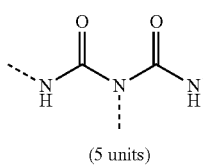

(5 units)

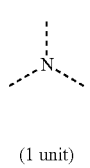

(1 unit)

-continued

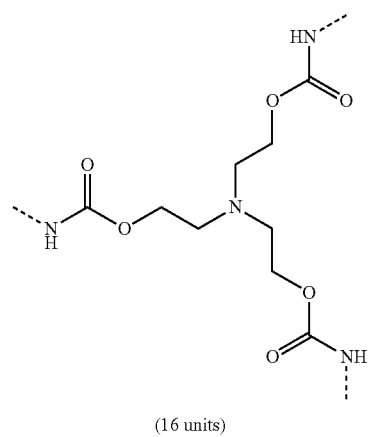

(16 units)

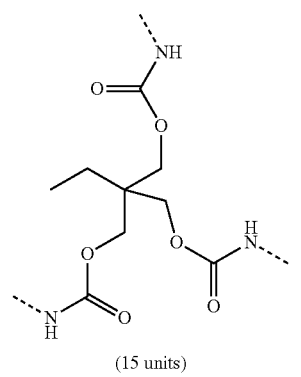

(15 units)

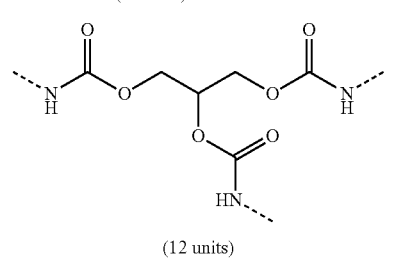

(12 units)

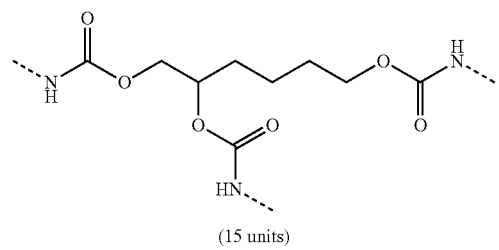

(15 units)

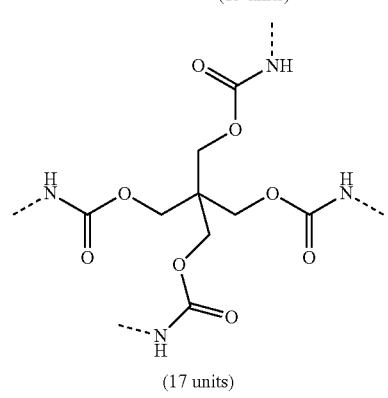

(17 units)

-continued (10 units)

(13 units)

(16 units)

The dotted lines indicate the bondings to the spacergroup S1.

The nature and structure of the spacergroups S1 or S2 is not particularly limited, either.

The spacergroups are comprised of units connected with each other. Typical units include: $CH_3$—, —$CH_2$—, —O—, —S—, —$NR^1$—, —CO—, —$CR^1$=, —N=, —$CR^1R^2$—, with $R^1$ and $R^2$ independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

$A-(CH_2)_4-U$    $A-(CH_2)_6-U$    $A-(CH_2)_8-U$
(4 units)           (6 units)           (8 units)

(13 units)

(13 units)

(8 units)           (8 units)

The dotted lines indicate the chemical bonding to either the group A or the group U.

Typical examples of useful spacer groups for S2 include:

(9 units)

(16 units)

(6 units)

The dotted lines indicate the chemical bonding to either the (meth)acrylate group or the group U. The number of the units to be counted according to the invention is given in brackets.

Specific examples of compound (A1) include:

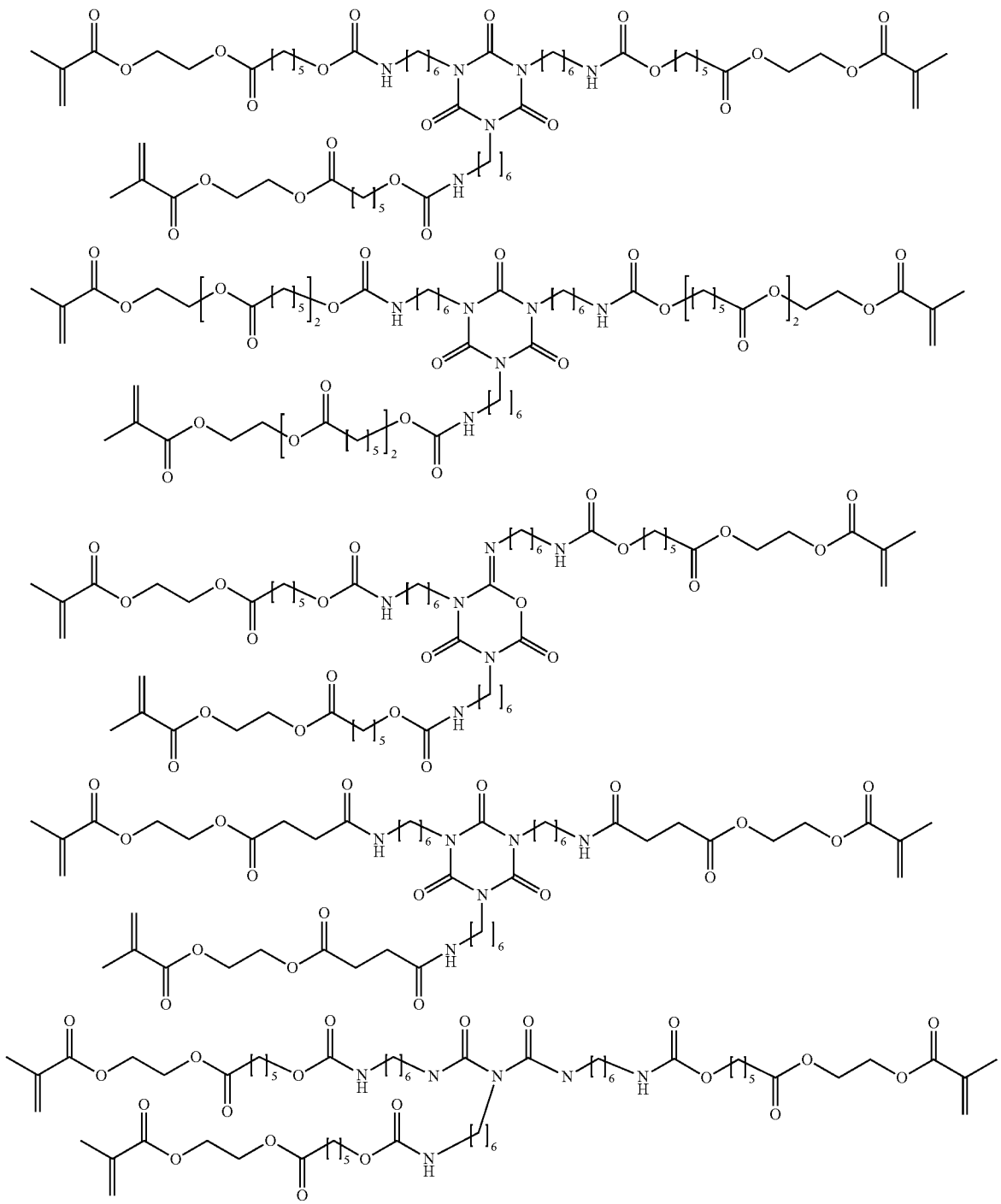

The molecular weight of compound (A1) is usually above about 900 g/mol or above about 950 g/mol or above about 1000 g/mol. Usually, the molecular weight of compound (A1) does not exceed a value of about 3000 or about 2700 or about 2500. Molecules having a molecular weight above about 1000 g/mol or above about 1100 g/mol are usually less volatile than molecules having a lower molecular weight and thus may contribute to providing a biocompatible composition.

Compound (A1) can be present in an amount of at least about 5 wt.-% or at least about 10 wt.-% or at least about 12 wt.-% with respect to the whole composition.

Compound (A1) can be present in an amount up to about 40 wt.-% or at least up to about 30 wt.-% or at least up to about 20 wt.-% with respect to the whole composition.

The nature of filler (B1) of the inventive composition is not particularly limited, either. The size of the filler particles should be such that a homogeneous mixture with the hardenable compound (A1) forming the hardenable resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate. Mixtures of two or more of these fillers can be used if desired.

The filler particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174 from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, cycloalkyl, hydroxy alkyl, aryl, hydroxy aryl, or amino alkyl functional silanes.

Suitable fumed silicas include for example, products sold under the tradename AEROSIL series OX-50, -130, -150, and -200, Aerosil R8200 available from Degussa AG, (Hanau, Germany), CAB-O-SIL M5 available from Cabot Corp (Tuscola, Ill.), and HDK types, e.g. HDK-H 2000, HDK H15; HDK H18, HDK H20 and HDK H30 available from Wacker.

Useful fluoroaluminosilicate glasses include silane treated fluoroaluminosilicate glass fillers, as described in U.S. Pat. No. 5,332,429, the disclosure of which is expressly incorporated by reference herein. For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 are preferred. The heavy metal oxide should be chosen such that undesirable colors or shading are not imparted to the hardened resin in which it is dispersed. For example, iron and cobalt would not be favored, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment filler (B1) comprises a nano-sized filler including nano-sized silica.

The nano-sized filler, especially the nano-sized silica is usually dispersed or dispersible within the hardenable resin matrix. The nano-sized particles used in the dental materials of the invention preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter. A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

The average surface area of the silica particles is preferably greater than about 15 $m^2/g$; more preferably greater than about 30 $m^2/g$.

Once dispersed in the resin, the nano-sized fillers and especially preferred the nano-sized silica particles are in a discrete (individual) and unassociated (i.e. non-agglomerated, non-aggregated) condition. Methods for dispersing the nano-sized fillers in the resin are described in U.S. Pat. No. 6,899,948 B2 and are included herein by reference. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The nano-sized silica particles which can be used in the dental materials of the invention are preferably substantially spherical and substantially non-porous. Although the silica is preferably essentially pure, it may contain small amounts of stabilizing ion such as ammonium and alkaline metal ions.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Surface-treating the nano-sized particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the nano-sized particles be modified over at least a portion of its surface with a surface treatment agent so that the stabilized particle can copolymerize or otherwise react with the hardenable resin during curing.

The nature and amount of filler(s) (B1) which can be used may not only have an effect on the viscosity of the composition but also may influence the aesthetic appearance (such as high gloss, high polish retention) and mechanical properties including hardness.

The filler (B1) is combined with appropriate hardenable compound(s) to form a dental composition of the invention.

Typically, the filler can be present in an amount of at least about 10 wt.-% or at least about 15 wt.-% or at least about 20 wt.-% with respect to the whole composition.

The filler can be present in an amount up to about 80 wt.-% or up to about 70 wt.-% or up to about 60 wt.-% with respect to the whole composition.

Dental materials of the invention can be chemically curable, heat curable or light curable compositions. Light curable materials should have an appropriate initiator system. Chemically curable materials can be auto-cured (e.g. via redox initiators). Alternatively, the materials of the invention can be hardened by a combination of auto- and light-cure.

For free radical polymerization (hardening), an initiator system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically are capable of generating free radicals for addition polymerization upon exposure to light energy having a wavelength between 200 and 800 nm.

A variety of visible, near UV and near-IR photoinitiator systems may be used for photopolymerization of free-radically polymerizable materials useful in the invention. For example, in free radical polymerization (hardening), a photoinitiator system can be selected from systems which initiate polymerization via a two component system of an amine and an α-diketone as described in U.S. Pat. No. 4,071,424, which is herein incorporated by reference. Alternatively, the resin can be combined with a three component or ternary photoinitiator system such as described in U.S. Pat. No. 5,545,676 which is incorporated herein by reference.

In the ternary photoinitator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313, U.S. Pat. No. 3,741,769, U.S. Pat. No. 3,808,006, U.S. Pat. No. 4,250,053 and U.S. Pat. No. 4,394,403, the iodonium salt disclosures of which are incorporated herein by reference. The iodonium salt can be a simple salt (e.g., containing an anion such as $Cl^-$, $Br^-$, $I^-$ or $C_6H_5SO_3^-$) or a complex salt (e.g., containing $BF_4^-$, $PF_6^-$, $SbF_6^-$ or $AsF_6^-$). Mixtures of iodonium salts can be used if desired.

Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 200 to 1200 nanometers, more preferably greater than 200 to 700 nanometers and most preferably greater than 200 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: $ACO(X)_bB$, where X is CO or $CR^5 R^6$, where $R^5$ and $R^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-di hydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione(camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incoporated herein by reference.

Alternatively, free-radical initiators useful in the invention include the class of acylphosphine oxides, as described in U.S. Pat. No. 4,737,593. Such acylphosphine oxides are of the general formula

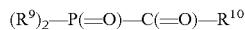

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl)titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye counterion complex initiators comprising a borate anion and a complementary cationic dye.

Borate salt photoinitiators are described, for example, in U.S. Pat. No. 4,772,530, U.S. Pat. No. 4,954,414, U.S. Pat. No. 4,874,450, U.S. Pat. No. 5,055,372, and U.S. Pat. No. 5,057,393, the disclosures of which are incorporated herein by reference.

Borate anions useful in these photointiators generally can be of the formula $R^1R^2R^3R^4B^-$ wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a redox reaction, are often referred to as "auto-cure catalysts." They are typically supplied as two-part systems in which the reactants are stored apart from each other and then combined immediately prior to use.

Organic peroxide compounds together with so-called activators are also suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]oxybutyl)-3,5-di-t-butylaniline as well as N,N-bis-(hydroxyalkyl)-3,4,5-trimethylaniline.

Further redox systems can be based on peroxides and barbituric acids and barbituric acid derivatives as described in US 2003/008967, DE 14 95 520 as well as the malonyl sulfamides described in EP 0 059 451. Preferred malonyl sulfamides are 2,6-dimethyl-4-isobutylmalonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide.

For further acceleration, the polymerization is in this case preferably carried out in the presence of heavy-metal compounds and ionogenic halogen or pseudohalogen. The heavy metal is suitably used in the form of soluble organic compounds. Likewise, the halide and pseudohalide ions are suitably used in the form of soluble salts, as examples there can be named the soluble amine hydrochlorides as well as quaternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, complexes of iron with 1,3-diketones, complexes of copper with 1,3- diketones (e.g. 1-phenylpentan-1,3-dion), copper naphthenate, copper acetate and iron naphthenate.

If the inventive dental compositions contain a redox initiator system comprising organic peroxide and activator, peroxide and activator are preferably present in parts physically separated from one another and are homogeneously mixed together only immediately before use. If organic peroxide, copper compound, halide and malonyl sulfamide and/or barbituric acid are present next to each other, it is particularly useful for the organic peroxide, malonyl sulfamide and/or barbituric acid and the combination of copper compound/halide to be present in three constituents physically separated from one another. For example, the combination of copper compound/halide, polymerizable monomers and fillers can be kneaded to a paste and the other components kneaded to two separate pastes each with a small quantity of fillers or in particular thixotropic auxiliaries, such as silanized silicic acid, and a plasticizer, for example phthalate. On the other hand, the polymerizable monomers can also be present together with organic peroxide and fillers. Alternatively, a distribution of organic peroxide, copper compound, halide and malonyl sulfamide and/or barbituric acid can be realized according to DE 199 28 238.

The initiator is preferably provided in the dental composition of the invention in an amount effective to initiate or enhance the rate of cure or hardening of the resin system.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 150° C. under normal conditions (23° C. and 1013 mbar) or at elevated pressure (e.g. at least about 2 bar). This procedure is preferred for initiating polymerization of materials occurring outside of the oral environment. Suitable initiators are organic peroxides (e.g. benzoyl peroxide) and inorganic peroxo compounds (e.g. sodium persulfate) or azo compounds, such as 4,4-azobisisobutyron itril.

Typically, the initiator can be present in an amount of at least about 0.1 wt.-% or at least about 0.5 wt.-% or at least about 1 wt.-% with respect to the whole composition.

The initiator can be present in an amount up to about 10 wt.-% or up to about 7.5 wt.-% or up to about 5 wt.-% with respect to the whole composition.

The inventive composition can also contain in addition at least one further hardenable compound (A2) being different from the hardenable compound (A1). Preferably, this further hardenable compound (A2) may have free radically active functional groups and include monomers, oligomers, and polymers having one or more ethylenically unsaturated groups.

In the class of hardenable resins having free radically active functional groups, suitable materials for use in the invention contain at least one ethylenically unsaturated bond, and are capable of undergoing addition polymerization. Such free radically polymerizable materials include mono-, di- or polyacrylates and methacrylates such as methyl acrylate. methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bisphenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

Preferred ethylenically unsaturated monomers are methacrylate and acrylate monomers, such as methyl(meth)acrylate, n- or i-propyl(meth)acrylate, n-, i- or tert-butyl(meth)acrylate and 2-hydroxy(meth)acrylate, 2-(meth)acryloxytetrahydrofuran, 2-(((alkylamino)carbonyl)oxy)ethyl(meth)acrylates, di(meth)acrylates of propanediol, butanediol, hexanediol, octanediol, nonanediol, decanediol and eicosanediol, tetrahydrofurfuryl(meth)acrylate, di(meth)acrylates of ethylene glycol, of polyethylene glycols and of polypropylene glycols, di(meth)acrylates of ethoxylated bisphenol A, for example 2,2'-bis(4-(meth)acryloxytetraethoxyphenyl)propanes, urethane(meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8(9)-tricyclo[5.2.1.0$^{2,6}$]decylmethyl triglycolate. Particularly suitable are 2,2-bis-4-(3-methacryloxy-2-hydroxypropoxy)phenylpropane (Bis-GMA), 2,2-bis-4-(3-methacryloxypropoxy)phenylpropane, triethylene glycol dimethacrylate (TEGDMA), and di(meth)acrylates of bishydroxymethyltricyclo-(5.2.1.0$^{2,6}$)decane.

Other hardenable compounds (A2) which can be added are urethane methacrylates being different from compound (A1) including low-molecular-weight compounds, such as 7,7,9-trimethyl-4,13-dioxo-3,14-dioxa-5,12-diazahexadecane-1,16-dioxy dimethacrylate (UDMA). Also useful are oligomeric or polymeric compounds, such as polyester urethane (meth)acrylates, polyether urethane(meth)acrylates, polycarbonate urethane(meth)acrylates and poly(meth)acrylate urethane(meth)acrylates. The molecular weight of these compounds is preferably less than 20,000 g/mol, particularly less than 15,000 g/mol and in particular less than 10,000 g/mol.

These ethylenically unsaturated monomers can be employed in the inventive dental compositions either alone or in combination with further ethylenically unsaturated monomers.

The hardenable compound (A2) can be present in an amount of at least about 0 wt.-% or at least about 5 wt.-% or at least about 10 wt.-% with respect to the whole composition.

The hardenable compound (A2) can be present in an amount up to about 84 wt.-% or up to about 80 wt.-% or up to about 70 wt.-% with respect to the whole composition.

The inventive composition can also contain further additives as component (D) or (Dx) if more than one additive is present, wherein "x" stands for the number of additives present. Typical additives include pigments and colorants. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole(2,6-di-tert-butyl-4-ethoxyphenol), 2,6-di-tert-butyl-4-(dimethyl-amino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethyl phenyl)-2H-benzotriazole, phenothiazine, and HALS (hindered amine light stabilizers). Such adjuvants may optionally comprise reactive functionality so that they will be copolymerized with the resin.

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

In order to increase the flexibility of the dental material, it is also possible to add soluble organic polymers including polyvinyl acetate, and copolymers thereof.

These additives do not need to be present at all. However, if they are present they are typically present in an amount of about 0.1 wt.-% or at least about 0.5 wt.-% or at least about 1 wt.-% with respect to the whole composition.

The further additives can be present in an amount up to about 25 wt.-% or up to about 20 wt.-% or up to about 15 wt.-% with respect to the whole composition.

Typically, the inventive composition can contain
the hardenable compound (A1) in an amount of about 5 wt.-% to about 40 wt.-% or of about 10 wt.-% to about 30 wt.-% or of about 12 wt.-% to about 20 wt.-%,
the filler (B1) in an amount of about 10 wt.-% to about 80 wt.-% or of about 15 wt.-% to about 70 wt.-% or of about 20 wt.-% to about 60 wt.-%,
the initiator (C1) in an amount of about 0.1 wt.-% to about 10 wt.-% or of about 0.5 wt.-% to about 7.5 wt.-% or of about 1 wt.-% to about 5 wt.-%,
a hardenable compound (A2) being different from hardenable compound (A1) in an amount of about 0 wt.-% to about 84 wt.-% or of about 5 wt.-% to about 80 wt.-% or of about 10 wt.-% to about 70 wt.-%, and
additives (Dx) in an amount of about 0 wt.-% to about 25 wt.-% or of about 0.5 wt.-% to about 20 wt.-% or of about 1 wt.-% to about 15 wt.-%; wt.-% with respect to the whole composition.

In certain embodiments the inventive composition fulfils at least one or more, sometimes all of the following parameters:
Compressive strength: at least about 270 MPa or at least about 280 MPa or at least about 290 MPa, determined as described in the experimental section below.
Flexural strength: at least about 70 MPa or at least about 80 MPa or at least about 90 MPa, determined according to ISO 4049 using test specimens having the dimensions 4 mm (height)*6 mm (width)*25 mm (length).
Deflection: at least about 1.1 mm or at least about 1.2 mm or at least about 1.4 mm, determined according to ISO 4049 using test specimens having the dimensions 4 mm (height)*6 mm (width)*25 mm (length).
Impact strength: at least about 8 kJ/m$^2$, or at least about 10 kJ/m$^2$ or at least about 12 kJ/m$^2$, determined according to ISO 179-1 (Charpy) using test specimens having the dimensions 4 mm (height)*6 mm (width)*50 mm (length).

In certain embodiments of the invention, the combination of the features flexural strength, deflection and impact strength has proven to be advantageous.

The invention also relates to a process of producing compound (A1) as described in the present text and to the product obtainable by such a process.

The process comprises the step of reacting an isocyanate group containing compound with a hydroxyl, an amino or a carboxylic group containing compound.

Useful isocyanate group containing compounds include:

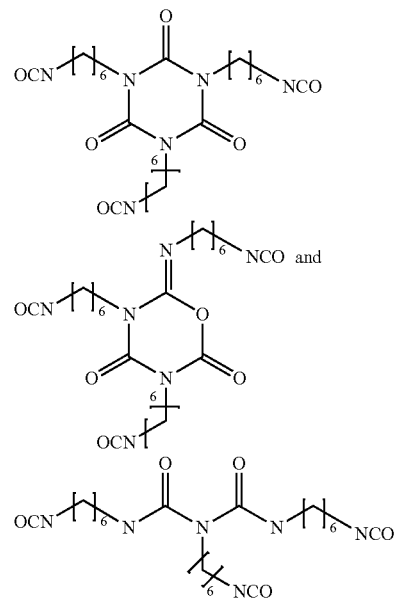

Those molecules are commercially available form e.g. Bayer AG under the trade name Desmodur™.

Other isocyanate group containing compounds can be easily obtained by reacting a polyhydroxy (e.g. trimethylol propane, glycerol, 1,2,6-hexanetriol, triethanolamine, pentaerythritol)/polycarboxylic (e.g. nitrilotriacetic acid, nitrilotripropionic acid, ethylene diamine tetraacetic acid)/polyamino (e.g. diethylene triamine, dipropylene triamine) functional compound with a stoichiometric amount of a diisocyanate (e.g. tetramethylene diisocyanate, hexamethylene diisocyanate, octamethylene diisocyanate, 4,4'-dicyclohexylmethane diisocyanate, 4,4'-diphenylmethane diisocyanate, p-xylylene diisocyanate, m-xylylene diisocyanate).

Useful hydroxyl group containing compounds include:

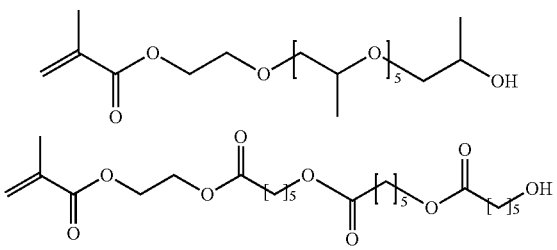

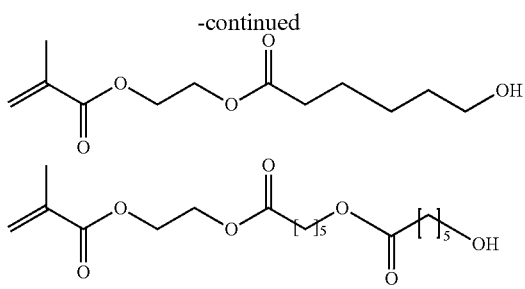

Useful carboxylic group containing compounds include:

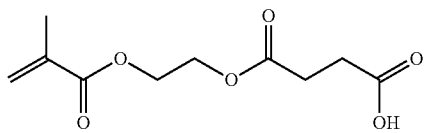

Those molecules are also commercially available from e.g. Daicel or Aldrich.

A useful amino group containing compound includes:

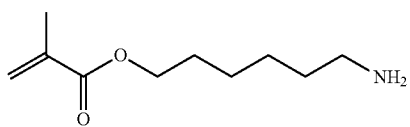

The synthesis of compound (A1) can take place in the presence of catalysts known from polyurethane chemistry, e.g. organotin compounds such as dibutyltin dilaurate or amine catalysts such as diazabicyclo[2.2.2]octane. Furthermore, the synthesis can take place both in the melt and in a suitable solvent which can be added before or during the synthesis. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Measured doses of the hydroxyl group, carboxylic acid group or amino group containing compound are added in one step or portion-wise to the NCO-containing compound accompanied by stirring and reacted for example in a temperature range from about −20° C. to about 160° C. or in a temperature range from about 0° C. to about 130° C. or a temperature range from about 20° C. to about 100° C. The reaction is usually completed within about 8 h to about 24 h.

The measurement of the isocyanate content can be done by the method described in DIN 53 185.

The reaction product can be isolated by methods know to the skilled person in the art including by removal of solvent under vacuum.

A preferred example of compound (A1) is the urethane (meth)acrylate described below. This molecule is obtainable by reaction of a certain isocyanurate with a certain hydroxy functional (meth)acrylate.

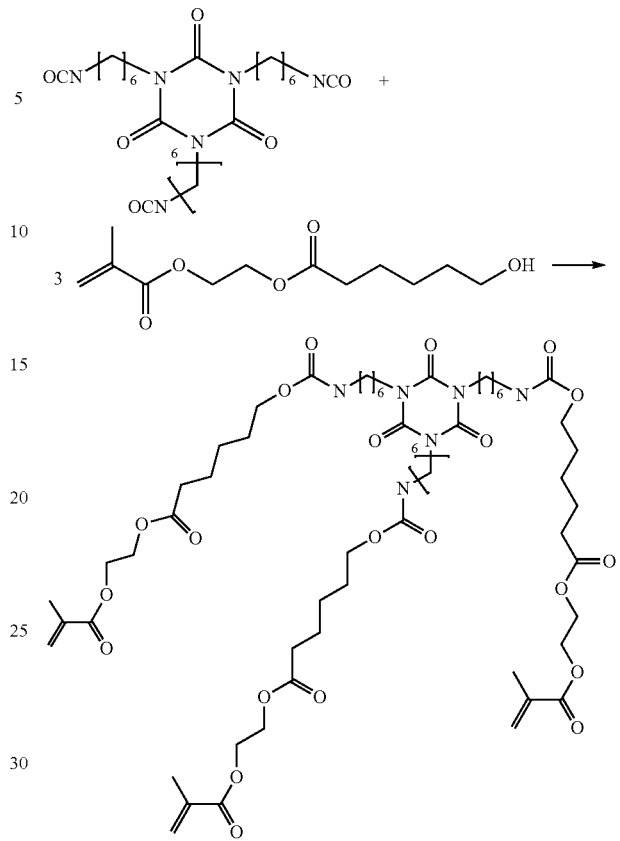

The invention also relates to a method of producing the inventive composition, the method comprising the step of mixing the hardenable compound (A1), the filler (B1) and the initiator (C1). Mixing of the components can be accomplished by hand using a spatula and a mixing pad or using a manually driven mixing device containing a static mixer.

Compositions useful in the invention can be prepared by simply mixing, including "safe light" conditions. Suitable inert solvents may be employed if desired. Any solvent may be used which does not react appreciably with the components of the inventive compositions. Examples of suitable solvents include ethyl acetate, acetone and ethanol.

In a further aspect, the invention relates to a kit of parts comprising a base part and a catalyst part, the base part comprising the hardenable compound (A1) and the catalyst part comprising the initiator (C1), wherein the filler (B1) and the additives (Dx) can be present either in the base part or the catalyst part, or the base part and the catalyst part.

In another aspect, the invention relates to a cartridge comprising two compartments (I) and (II) separated from each other, the compartments having a rear and a front end, wherein the front ends can be opened and can be connected to a static mixing tip, wherein compartment (I) contains the hardenable compound (A1) and compartment (II) contains the initiator (C1). Filler (B1) and the additives (Dx) can be present either in compartment (I) or compartment (II), or in compartment (I) and compartment (II). The volume ratio of compartment (I) to compartment (II) is typically within a range of about 1:1 to about 10:1.

Useful cartridges are described in US 2007/0090079 or U.S. Pat. No. 5,918,772, the disclosure of which is incorporated by reference. Cartridges which can be used are commercially available from SulzerMixpac AG (Switzerland).

Useful static mixing tips are described in US 2006/0187752 or in U.S. Pat. No. 5,944,419, the disclosure of which is incorporated by reference. Mixing tips which can be used are commercially available from SulzerMixpac AG (Switzerland).

Furthermore, the invention relates to a method of using the hardenable compound (A1) as described in the text of the invention for producing a dental composition, the method comprising the step of adding the hardenable compound (A1) to a filler and to a suitable initiator.

The dental compositions of the invention can be used for example, as dental adhesives, artificial crowns, anterior or posterior fillings, casting materials, cavity liners, cements, coating compositions, mill blanks, orthodontic devices, restoratives, prostheses, and sealants. In a preferred aspect, the dental material is a temporary and long term crown and bridge material. The temporary and long term crown and bridge materials of the invention can be placed directly in the mouth and cured (hardened) in situ, or alternatively, may be fabricated into a prosthesis outside the mouth and subsequently adhered in place inside the mouth.

In another aspect, the invention relates to a method of producing a temporary or long term crown or bridge, the method comprising the steps of placing the composition as described in the text of the invention into the moulds of a set dental impression material. The dental impression material can be an alginate, a silicone (VPS) or polyether impression dental material.

Commercially available alginate impression materials include Palgat™ (3M ESPE). Commercially available silicone impression materials include Express™, Imprint™ and Position™ (3M ESPE). Commercially available polyether impression materials include Impregum™ (3M ESPE).

A typical process in the dental practice comprises one or more steps of
a) preparing or shaping a hard tooth structure for impressioning,
b) making an impression of hard tooth structure using a dental impression material, thereby obtaining a negative mould of the tooth structure,
c) waiting until the dental impression material is set,
d) removing the set dental impression material from the hard tooth structure,
e) preparing or shaping the hard tooth structure for the final restoration
f) placing the curable composition of the invention into the negative mould obtained in steps a-d),
g) repositioning the filled negative mould of step f) onto the prepared or shaped tooth structure of step e),
h) waiting until the curable composition is at least partially cured, so that the composition can be removed from the prepared or shaped tooth structure without leaving residues of the composition on the prepared or shaped tooth structure,
i) removing the composition of step h) from the set impression material,
k) adhesively fixing the removed composition of step i) onto the prepared or shaped tooth structure using a dental cement.

The following examples are given to illustrate, but not limit, the scope of this invention. Unless otherwise indicated, all parts and percentages are by weight.

EXAMPLES

Preparation of Specimens:

The material was applied into the respective metal moulds using a Garant™ II 10:1 cartridge equipped with a static mixer (SulzerMixpac Company). Cure was effected under pressure between plastic foil (Hostaphan™ RN75) and plexiglass plates for 1 h at 23° C. Then the press, plexiglass plates and foil were removed and the specimens within the moulds were subject to post-cure at 36° C. under demineralised water for 23 h. The moulds were removed immediately before measurement.

Measurements

Compressive Strength

Compressive strength was measured according to DIN 53454 (ISO 9917 2001) using cylindrical specimens with a diameter of 4 mm and a height of 8 mm.

Flexural Strength, Deflection

A three point flexural test comparable to ISO 4049 was conducted to determine flexural strength and deflection. The only deviation to the measurement instructions given in ISO 4049 was the size of specimens. For the measurements reported in the present invention the test specimens had a size of 4×6×25 mm.

Impact Strength

Impact strength was measured according to ISO 179-1 (Charpy) using unnotched specimens (test specimen size: 4×6×50 mm) and a 0.5 J pendulum.

Compositions

Abbreviations

TABLE 1

| Name | Description | Availability |
|---|---|---|
| NADZ | 42.5% silanized (6%) silica nanofiller (50 nm) dispersed in ethoxylated bisphenol A dimethacrylate | cf. U.S. Pat. No. 6,899,948 |
| HDK H-2000 | fumed silica | Wacker-Chemie GmbH |
| Cu-procetonat | Copper(II) bis(1-phenylpentan-1,3-dione) complex | |
| Ionol | 2,6-ditert.butyl-4-methylphenol | Raschig AG |
| BZPBS | 1-Benzyl-5-phenyl-barbituric acid | Chemische Fabrik Berg GmbH |
| TBPIN | tert. Butylperoxy-3,5,5-trimethylhexanoate | Peroxidchemie GmbH & Co KG |
| Z-Acetat | ethoxylated Bisphenol A diacetate | |
| Amin-HCl | dibutylphenylethyl-amine hydrochloride | |
| Sr-Glass I | strontium containing glass filler (<3 μm) | Schott Glaswerke |
| Sr-Glass II | strontium containing glass filler (3% silanated; <3 μm) | Schott Glaswerke |

TABLE 1-continued

| Name | Description | Availability |
|---|---|---|
| D-Zethacrylat | ethoxylated Bisphenol A dimethacrylate | |
| DESMA | urethane(meth)acrylate | cf. synthesis below |

Typical Synthesis of Compound (A1)—(Example 1; DESMA)

To a mixture of 65.0 g Desmodur N3300, 29.9 mg Ionol, 68.6 mg dibutyl tin dilaurate (DBTDL) and 21.8 g ethyl acetate, 84.7 g Placcel FM1 D were added under dry air within 1 h. Throughout the reaction, the temperature was kept between 50-60° C. After the addition of Placcel FM1D, the mixture was stirred at 50° C. for 12 h and then allowed to cool to room temperature under continued stirring over night. Quantitative reaction of the isocyanate groups was determined according to DIN 53185. The obtained reaction product was used without further isolation or purification.

The other compounds (A1) used in Examples 2 to 5 and the hardenable compound used in the Comparative Example were prepared accordingly as described in more detail in Table 2. The chemical structures of the components used are given in Table 3.

TABLE 2

| | Isocyanate [g] | Hydroxy-/carboxylic acid functional (meth)acrylate [g] | Ionol [mg] | Dibutyl tin dilaurate [mg] | Reaction conditions |
|---|---|---|---|---|---|
| Example 1 and Example 6 (DESMA) | DESMODUR N3300 65.0 g | Caprolactone-MA (Placcel FM1D) 84.7 g | 29.9 mg | 68.6 mg | See above |
| Example 2 | DESMODUR N3300 57.0 g | Tone M100-MA 103.5 g | 19.2 mg | 48.0 mg | See above |
| Example 3 | DESMODUR XP2410 85.1 g | Caprolactone-MA 118.8 g | 40.5 mg | 101.2 mg | See above |
| Example 4 | DESMODUR N3300 115.4 g | Succinic acid MA 147.7 g | 116.6 mg | 166.6 mg | See above |
| Example 5 | DESMODUR N100 106.4 g | Caprolactone-MA 138.0 g | 48.5 mg | 121.3 mg | See above |
| Comparative Example | DESMODUR N3300 57.0 g | HEMA 39.1 g | 19.2 mg | 48.0 mg | See above, synthesis without ethyl acetate |

TABLE 3

| | Isocyanate | Hydroxy-/carboxylic acid functionalized (meth)acrylate |
|---|---|---|
| Compound (A1) of Example 1 and Example 6 | DESMODUR N3300 | Caprolactone-MA/Placcel FM 1D |

TABLE 3-continued

| | Isocyanate | Hydroxy-/carboxylic acid functionalized (meth)acrylate |
|---|---|---|
| Compound (A1) of Example 2 | DESMODUR N3300 | Tone M 100-MA |
| Compound (A1) of Example 3 | DESMODUR XP 2410 | Caprolactone-MA/Placcel FM 1D |
| Compound (A1) of Example 4 | DESMODUR N3300 | Succinic acid-MA |

TABLE 3-continued

| | Isocyanate | Hydroxy-/carboxylic acid functionalized (meth)acrylate |
|---|---|---|
| Compound (A1) of Example 5 | DESMODUR N 100 | Caprolactone-MA/Placcel FM 1D |
| Hardenable compound of Comparative Example | DESMODUR N3300 [570] | HEMA |

Typical Preparation of Compositions of Examples 1-6 and Comparative Example

The compositions described below were generally prepared as follows:

Solution A:

Cu-procetonat, Amin-HCl, and Ionol were dissolved in ethyl acetate and added to D-Zethacrylat and DESMA with stirring at room temperature. Amounts are given in Tables 4-10. After a homogeneous mixture was obtained. The ethyl acetate was removed under vacuum.

Paste A:

Pigments, solution A, HDK-H 2000, and fillers (see Tables 4-10) were mixed in a three-arm laboratory kneader. Residual filler agglomerates were homogenized in a ceramic three-roller mill.

Paste B:

TBPIN, BZPBS, Z-Acetat, Sr-Glass I, and HDK-H 2000 were mixed in a three-arm laboratory kneader. Residual filler agglomerates were homogenized in a ceramic three-roller mill.

Then Paste A and Paste B were filled into the respective compartments of a 10:1 SulzerMixpac™ cartridge.

In Tables 4-9 the composition of Examples 1 to 6 and in Table 10 the composition of a Comparative Example are given.

Example 1

TABLE 4

| Component | Percent by weight [%] |
|---|---|
| Paste A: | |
| D-Zethacrylat | 52.6 |
| DESMA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigments | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

Example 2

TABLE 5

| Component | Percent by weight [%] |
|---|---|
| Paste A: | |
| D-Zethacrylat | 52.6 |
| DESMODUR N3300/TONE M100-MA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigments | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

Example 3

TABLE 6

| Component | Percent by weight [%] |
|---|---|
| Paste A: | |
| D-Zethacrylat | 52.6 |
| DESMODUR XP2410/Caprolactone-MA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigments | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

Example 4

TABLE 7

| Component | Percent by weight [%] |
|---|---|
| Paste A: | |
| D-Zethacrylat | 52.6 |
| DESMODUR N3300/Succinic acid-MA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigments | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

Example 5

TABLE 8

| Component | Percent by weight [%] |
|---|---|
| Paste A: | |
| D-Zethacrylat | 52.6 |
| DESMODUR N100/Caprolactone-MA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigments | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

Example 6

TABLE 9

| Component | Percent by weight [%] |
|---|---|
| Paste A: | |
| D-Zethacrylat | 21.4 |
| DESMA | 13.4 |
| NADZ | 56.2 |
| HDK H-2000 | 8.6 |
| Cu-procetonat | 0.001 |
| Amin-HCl | 0.18 |
| Ionol | 0.04 |
| Pigments | 0.05 |
| Sum: | 100.0 |
| Paste B: | |
| BZPBS | 10.0 |
| TBPIN | 0.3 |

TABLE 9-continued

| Component | Percent by weight [%] |
|---|---|
| HDK H-2000 | 10.0 |
| Z-Acetat | 79.7 |
| Sum: | 100.0 |

Comparative Example

Desmodur N3300/HEMA corresponds essentially to the synthesis of HMDIT(MA$^1$)$_3$ described by Sumita B. Mitra in "Dental composites prepared from resin matrices containing ethylencially unsaturated carbamoyl isocyanorates in Polymer Preprints, Division of Polymer Chemistry, American Chemical Society, vol. 38, no. 2. pages 103-140.

TABLE 10

| Component | Percent by weight [%] |
|---|---|
| Paste A: | |
| D-Zethacrylat | 52.6 |
| DESMODUR N3300/HEMA | 12.8 |
| Sr-Glass II | 24.11 |
| HDK H-2000 | 10.0 |
| Cu-procetonat | <0.001 |
| Amin-HCl | 0.15 |
| Ionol | 0.03 |
| Hydrochinonmonomethylether | <0.001 |
| Pigmente | 0.26 |
| Sum: | 100.0 |
| Paste B: | |
| BZPBS | 10.0 |
| TBPIN | 0.3 |
| Sr-Glass I | 26.5 |
| Z-Acetat | 63.2 |
| Sum: | 100.0 |

The compositions described above were tested with respect to their mechanical properties. The test results are given in Table 11 below.

TABLE 11

| Example | Molar Mass of component A1 [g/mol] | Flexural Strength [MPa] | Deflection [mm] | Impact Strength [kJ/m$^2$] | Compression Strength [MPa] |
|---|---|---|---|---|---|
| 1 | 1303 | 98.4 | 1.52 | 13.6 | 294.8 |
| 2 | 1602 | 91.3 | 1.25 | 9.2 | 329.3 |
| 3 | 1280 | 100.2 | 1.63 | 11.7 | 304.9 |
| 4 | 1106 | 101.4 | 1.44 | 10.9 | 291.4 |
| 5 | 1306 | 107.2 | 1.65 | 12.4 | 295.9 |
| 6 | 1303 | 96.1 | 1.38 | 13.5 | 314.9 |
| Comparative Example | 960 | 90.8 | 1.04 | 6 | 263.9 |

The invention claimed is:
1. A dental composition comprising
a) a hardenable compound (A1),
b) a filler (B1) and
c) an initiator (C1) being able to initiate hardening of compound (A1), compound (A1) having the structure A-(-S1-U-S2-MA)$_n$, with
A being a connector element comprising at least one unit,
S1 being a spacergroup comprising at least 4 units connected with each other,
S2 being a spacergroup comprising at least 4 units connected with each other,
the units of A, S1 and S2 being independently selected from CH$_3$—, CH$_2$—, —O—, —S—, —NR$^1$—, —CO—, —CR$^1$=,

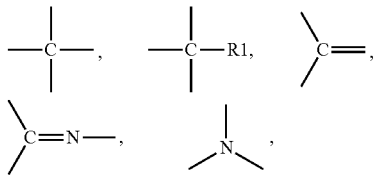

—N=, —CR$^1$R$^2$—, with R$^1$ and R$^2$ independently selected from hydrogen, alkyl, substituted alkyl, alkenyl, cycloalkyl, substituted cycloalkyl arylalkyl, aryl or substituted aryl, wherein these units can form linear, branched or cyclic structures such as alkyl, cycloalkyl, aryl, ester, urethane or amide groups,
U being an urethane, urea or amide group connecting spacergroups S1 and S2,
MA being an acrylate or methacrylate group and
n being 3 to 6.
2. The dental composition according to claim 1, wherein the filler (B1) comprises a nano-sized filler having a particle size of less than about 200 nm.
3. The dental composition according to claim 1, wherein the initiator is a light-curing, redox-curing or heat-curing initiator.
4. The dental composition according to claim 1 characterized by at least one of the following parameters:
Compressive strength: at least about 270 MPa, determined according to DIN 53454 (ISO 9917 2001) using cylindrical specimens with a diameter of 4 mm and a height of 8 mm,
Flexural strength: at least about 70 MPa, determined according to ISO 4049 using test specimens having the dimensions 4 mm (height)*6 mm (width)*25 mm (length),
Deflection: at least about 1.1 mm, determined according to ISO 4049 using test specimens having the dimensions 4 mm (height)*6 mm (width)*25 mm (length),
Impact strength: at least about 8 kJ/m$^2$, determined according to ISO 179-1 (Charpy) using test specimens having the dimensions 4 mm (height)*6 mm (width)*50 mm length),
Molecular weight of A1 being at least 1000.
5. The dental composition according to claim 1 comprising in addition additives (Dx) and a radically polymerizable compound (A2), the radically polymerizable compound (A2) being different from compound (A1) and/or the additives (Dx).
6. The dental composition according to claim 5, wherein
the hardenable compound (A1) is present in an amount of about 5 wt.-% to about 40 wt.-%,
the filler (B1) is present in an amount of about 10 wt.-% to about 80 wt.-%,
the initiator (C1) is present in an amount of about 0.1 wt.-% to about 10 wt.-%,
the hardenable compound (A2) is present in an amount of about 0 wt.-% to about 84 wt.-%, and
the additives (Dx) are present in an amount of about 0 wt.-% to about 2.5 wt.-%;
wt.-% with respect to the whole composition.
7. The dental composition according to claim 1, wherein compound (A1) is selected from the group consisting of

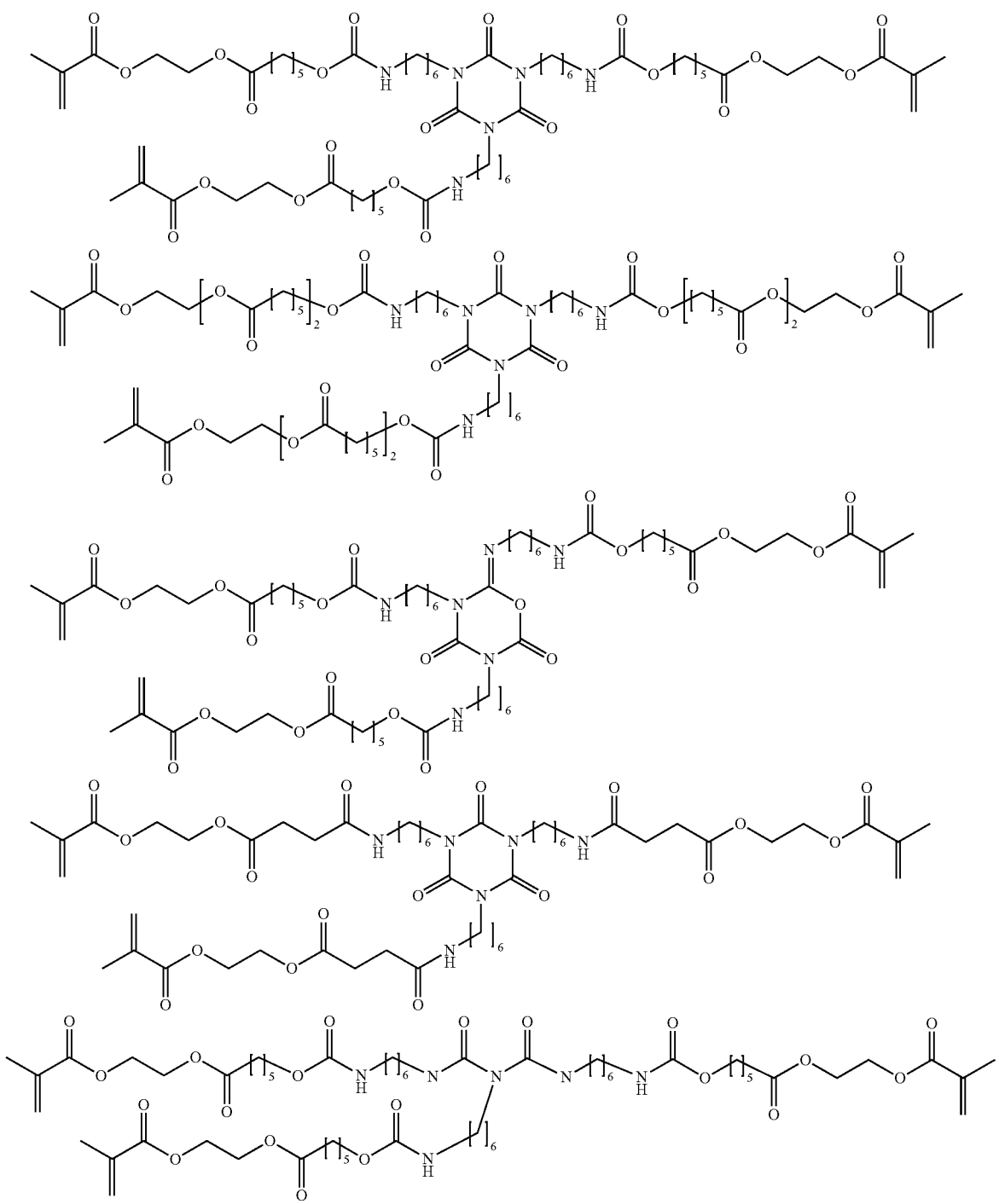

and mixtures thereof.

8. A method of producing the dental composition according to claim 1, the method comprising the step of mixing the hardenable compound (A1), the filler (B1) and the initiator (C1).

9. The method according to claim 8, further comprising producing the hardenable compound (A1) by reacting an isocyanate group containing compound selected from the group consisting of

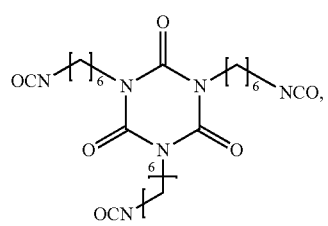

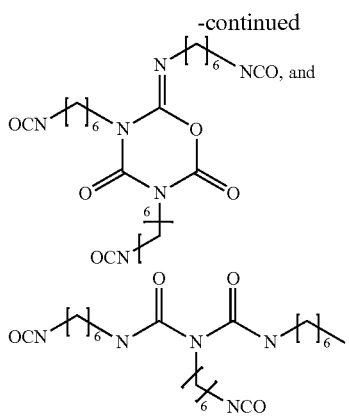

with a hydroxyl/ amino/ carboxyl group containing compound selected from the group consisting of

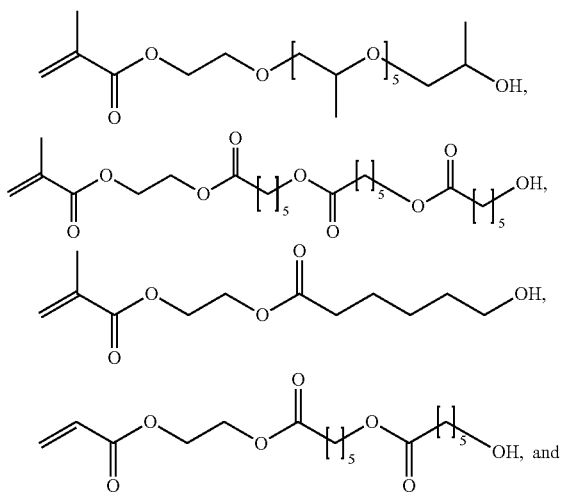

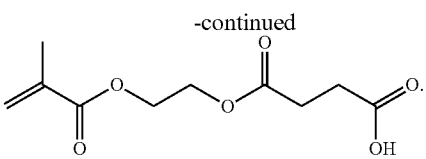

10. An article comprising the dental composition of claim 1 that is any of dental adhesives, casting materials, cements, coating compositions, sealants, or impression materials.

11. A method of producing a temporary or long term crown and bridge, comprising the step of placing the dental composition of claim 1 into the moulds of a set dental impression material.

12. A kit of parts comprising a base part and a catalyst part, the base part comprising the hardenable compound (A1) and the catalyst part comprising the initiator (C1), wherein the filler (B1) can be present either in:

(1) the base part or the catalyst part, or (2) the base part and the catalyst part;

wherein compound (A1), fillet (B1) and initiator (C1) are as described in claim 1.

13. The kit of parts according to claim 12, contained in a cartridge comprising two compartments (I) and (II) separated from each other, the compartments having a rear and a front end, wherein the front ends can be opened and can be connected to a static mixing tip, wherein compartment (I) contains the base part and compartment (II) contains the catalyst part.

14. An article comprising the dental composition of claim 1 that upon hardening is any of artificial crowns, temporary and long-term temporary crown and bridge materials, anterior or posterior fillings, cavity liners, mill blanks, orthodontic devices, restoratives, or prostheses.

* * * * *

UNITED STATES PATENT AND TRADEMARK OFFICE
CERTIFICATE OF CORRECTION

PATENT NO. : 8,329,776 B2
APPLICATION NO. : 12/666833
DATED : December 11, 2012
INVENTOR(S) : Reinhold Hecht It is certified that error appears in the above-identified patent and that said Letters Patent is hereby corrected as shown below:

Column 1
Line 30, delete "ethylencially" and insert -- ethylenically --, therefor.
Line 31, delete "isocyanorates" and insert -- isocyanurates --, therefor.
Line 35, delete "artifical" and insert -- artificial --, therefor.

Column 13
Line 52, delete "photoinitator" and insert -- photoinitiator --, therefor.

Column 14
Lines 49-50, delete "2,4-di hydroxybenzophenone," and insert
    -- 2,4-dihydroxybenzophenone, --, therefor.

Column 15
Line 15, delete "incoporated" and insert -- incorporated --, therefor.

Column 16
Line 1, delete "photointiators" and insert -- photoinitiators --, therefor.
Line 44, delete "([beta]oxybutyl)" and insert -- ([beta]-oxybutyl) --, therefor.
Line 51, delete "2,6-dibutyl4-" and insert -- 2,6-dibutyl-4- --, therefor.
Line 52, delete "2,6-dimethyl4-" and insert -- 2,6-dimethyl-4- --, therefor.
Line 53, delete "2,6-dioctyl4-" and insert -- 2,6-dioctyl-4- --, therefor.

Column 17
Line 1, delete "-dion)," and insert -- -dione), --, therefor.
Line 38, delete "4,4-azobisisobutyron itril." and insert -- 4,4-azobisisobutyronitril. --, therefor.

Column 18
Lines 62-63, delete "Neazopon" and insert -- Neozapon --, therefor.

Signed and Sealed this
Twenty-sixth Day of February, 2013

Teresa Stanek Rea
*Acting Director of the United States Patent and Trademark Office*

Column 19
Lines 10-11, delete "methacryloxyethyl phenyl)" and insert -- methacryloxyethylphenyl) --, therefor.

Column 20
Line 41, delete "form" and insert -- from --, therefor.

Column 23
Line 45, after "restoration" insert -- , --.

Column 25
Line 14, delete "FM1 D" and insert -- FM1D --, therefor.

Column 30
Line 54, delete "Hydrochinonmonomethylether" and insert -- Hydroquinone monomethyl ether --, therefor.

Column 31
Line 16, delete "Hydrochinonmonomethylether" and insert -- Hydroquinone monomethyl ether --, therefor.
Line 43, delete "Hydrochinonmonomethylether" and insert -- Hydroquinone monomethyl ether --, therefor.

Column 32
Line 8, delete "Hydrochinonmonomethylether" and insert -- Hydroquinone monomethyl ether --, therefor.
Line 34, delete "Hydrochinonmonomethylether" and insert -- Hydroquinone monomethyl ether --, therefor.

Column 33
Line 14, delete "ethylencially" and insert -- ethylenically --, therefor.
Line 14, delete "isocyanorates" and insert -- isocyanurates --, therefor.
Line 29, delete "Hydrochinonmonomethylether" and insert -- Hydroquinone monomethyl ether --, therefor.

Column 34
Line 3, in Claim 1, delete "S1and" and insert -- S1 and --, therefor.
Line 4, in Claim 1, delete "$CH_3$—,$CH_2$—," and insert -- $CH_3$—, —$CH_2$—, --, therefor.
Line 46, in Claim 4, delete "haying" and insert -- having --, therefor.
Line 48, in Claim 4, delete "length)," and insert -- (length), --, therefor.
Line 64, in Claim 6, delete "2.5" and insert -- 25 --, therefor.

Column 38
Line 24, in Claim 12, delete "fillet" and insert -- filler --, therefor.